United States Patent [19]

Carr et al.

[11] Patent Number: 5,106,845
[45] Date of Patent: Apr. 21, 1992

[54] CALCIUM ANTAGONISTS

[75] Inventors: Albert A. Carr; Hsien C. Cheng; John M. Kane, all of Cincinnati, Ohio

[73] Assignee: Merrell Dow Pharmaceuticals Inc., Cincinnati, Ohio

[21] Appl. No.: 457,997

[22] Filed: Jan. 10, 1990

[51] Int. Cl.$^5$ .................. A61K 31/55; A61K 31/505; A61K 31/50; A61K 31/415

[52] U.S. Cl. .................. 514/218; 514/219; 514/252; 514/254; 514/255; 514/266; 514/321; 514/326; 514/393; 514/398; 514/401; 514/402

[58] Field of Search ............... 514/183, 186, 219, 221, 514/255, 260, 321, 326, 393, 398, 252, 254, 718, 322, 401, 402; 540/470, 473, 553, 567

[56] References Cited

U.S. PATENT DOCUMENTS

| | | | |
|---|---|---|---|
| 3,840,554 | 10/1974 | Wittekind et al. | 548/350 |
| 4,234,894 | 11/1980 | Rasmussen | 514/409 |
| 4,243,667 | 1/1981 | Rasmussen | 514/409 |
| 4,829,065 | 5/1989 | Pascal et al. | 514/255 |

FOREIGN PATENT DOCUMENTS 0255710  10/1988  European Pat. Off.
7736243  6/1978  France.

OTHER PUBLICATIONS

Goodman and Gillman's Pharmacological Basis of Therapeutics (MacMillan, N.Y., New York, 1985) pp. 820–822.

Primary Examiner—Mukund J. Shah
Assistant Examiner—E. C. Ward

[57] ABSTRACT

The present invention is directed to a new class of cyclic guanidines of the formula:

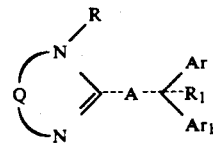

in which Q is represented by a substituent selected from the group consisting of $(CH_2)_n$ in which n is an integer from 2–10,

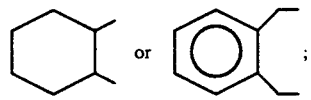

A is a substituent selected from the group consisting of —NH—$(CH_2)_m$ in which m is an integer from 0–5, a piperidino substituent, or a piperazino substituent; both Ar and Ar$_1$ are each independently represented by a phenyl ring, each of which may be optionally substituted with up to 3 substituents, each selected from the group consisting of halogen, $C_{1-4}$ alkyl, $C_{1-4}$ alkoxy, and trifluoromethyl; and R is represented by either hydrogen or a $C_{1-4}$ alkyl; $R_1$ is represented by hydrogen or a $C_{1-4}$ alkyl; the optional isomers and tautomers thereof; and the pharmaceutically acceptable acid addition salts thereof, and their use as calcium antagonists.

1 Claim, No Drawings

CALCIUM ANTAGONISTS

The present invention is directed to a new class of cyclic guanidines and to their use as calcium antagonists. Another aspect of the invention is directed to the discovery of a new use for a group of known cyclic guanidines.

In accordance with the present invention, a new class of cyclic guanidine derivatives have been discovered which are useful as calcium antagonists. These compounds can be described by the following formula:

FORMULA I

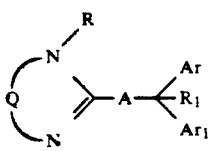

in which Q is represented by a substituent selected from the group consisting of $(CH_2)_n$ in which n is an integer from 2-10,

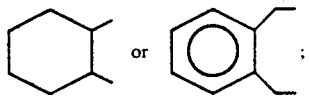

A is a substituent selected from the group consisting of $-NH-(CH_2)_m$ in which m is an integer from 0-5, a piperidino substituent, or a piperazino substituent; both Ar and $Ar_1$ are each independently represented by a phenyl ring each of which may be optionally substituted with up to 3 substituents, each selected from the group consisting of halogen, $C_{1-4}$ alkyl, $C_{1-4}$ alkoxy, hydroxy, and trifluoromethyl; and R is represented by hydrogen or $C_{1-4}$ alkyl $R_1$ is represented by hydrogen or $C_{1-4}$ alkyl; the optical isomers and tautomers thereof; and the pharmaceutically acceptable acid addition salts thereof; with the provisos that: 1) when Q is represented by $(CH_2)_{2,3}$, or 4, then A is not represented by $N-(CH_2)_o$; and 2) when Q is represented by $(CH_2)_2$ and R is a $C_{1-4}$ alkyl; then A is not $N-(CH_2)$.

Those compounds which are encompassed by the two provisos immediately above are known in the art as hypoglycemic agents. It has been discovered that these known compounds are also useful as calcium antagonists.

Throughout the rest of the specification, any reference to the compounds of Formula I should be considered as encompassing both those known cyclic guanidines as well as the new class of cyclic guanidines. Thus, those portions of the specification in which methods are taught for making the compounds, their use as calcium antagonists, and means for formulating their pharmaceutical compositions, are equally applicable to both the known cyclic guanidines and to the new class of cyclic guanidines encompassed by the present invention.

Calcium antagonists have been discovered to be useful in the treatment of a variety of disease states. They have been found to be useful in the treatment of cardiac arrhythmias, angina, depression, hypertension, epilepsy, and mania. They have also been found to exhibit a vasodilatory effect and therefore are useful in the treatment of congestive heart failure. More recently they have been discovered to be useful in preventing the phenomenon of calcium overload which is associated with reperfusion therapy. The compounds of Formula I are also useful for these therapeutic indications.

As used in this application:

a) the term "halogen" refers to a fluorine, chlorine, or bromine atom;

b) the term "$C_{1-4}$ alkyl" refers to a branched or straight chained alkyl group containing from 1-4 carbon atoms, such as methyl, ethyl, n-propyl, isopropyl, n-butyl, isobutyl, and t-butyl;

c) the term "$C_{1-4}$ alkoxy" refers to a straight or branched alkoxy group containing from 1-4 carbon atoms, such as methoxy, ethoxy, n-propoxy, isopropoxy, n-butoxy isobutoxy, and t-butoxy;

d) the term "piperidino" refers to the following substituent;

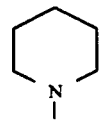

e) the term "piperazino" refers to the following substituent;

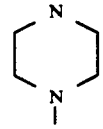

f) the term "trifluoromethyl" refers to the following substituent: $-CF_3$;

g) the term "hydroxy" refers to the following substituent $-OH$, and;

h) the terms "phenyl" and "phenyl ring" refer to the following substituent.

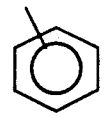

The expression "pharmaceutically acceptable acid addition salts" is intended to apply to any nontoxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate Illustrative organic acids which form suitable salts include the mono-, di- and tricarboxylic acids Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methane sulfonic acid and 2-hydroxy-ethane sulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

Some of the compounds of Formula I contain asymmetric centers. Any reference in this application to one of the compounds represented by Formula I is meant to encompass either a specific optical isomer or a mixture of enantiomers. The specific optical isomers can be separated and recovered by techniques known in the art such as chromatography on chiral stationary phases or resolution via chiral salt formation and subsequent separation by selective crystallization.

All of the compounds of Formula I contain the guanidine moiety. This moiety may exist in any of the tautomeric forms depicted below. The present invention should be considered as encompassing compounds existing in either of these tautomeric forms:

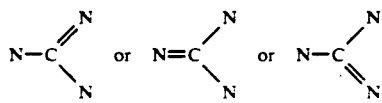

As noted above for the compounds of Formula I, Ar and Ar$_1$ can be independently represented by either a substituted or an unsubstituted phenyl ring. Both phenyl rings can be either substituted, unsubstituted, or only one of the phenyl rings may be substituted. If the phenyl ring is substituted, there can be up to 3 substitutions occurring on either phenyl ring. These substitutions can be the same or different. These substitutions can occur at any of the ortho, meta, or para positions.

In those compounds of Formula I, wherein A is represented by a piperidino substituent, the 1-position of the piperidino ring should be bonded to the diamino-substituted carbon of Formula I and the 4-position of the piperidino ring should be bonded to the diphenyl substituted carbon of Formula I. The piperidino ring should remain unsubstituted otherwise. When A is represented by a piperazino ring, then one of the nitrogen atoms in the piperazino ring should be bonded to the diamino substituted carbon of Formula I and the other nitrogen atom of the piperazino ring should be bonded to the diphenyl substituted carbon of Formula I. The piperazino ring should remain otherwise unsubstituted.

Representative members of the new class of cyclic guanidines encompassed by Formula I include:
a) 2-(2,2-Diphenylethylamino)imidazoline.
b) 2-(3,3-Diphenylpropylamino)imidazoline.
c) 2-(3,3-Diphenylpropylamino)-1-methylimidazoline.
d) 2-(4,4-Diphenylbutylamino)-1-methylimidazoline.
e) 2-(2,2-Diphenylethylamino)-1,4,5,6-tetrahydropyrimidine.
f) 2-[3,3-Bis-(4-fluorophenyl)propylamino]-1,4,5,6-tetrahydropyrimidine.
g) 2-(3,3-Diphenylpropylamino)-1,4,5,6-tetrahydropyrimidine.
h) 2-(2,2-Diphenylethylamino)-1-methyl-1,4,5,6-tetrahydropyrimidine.
i) 2-(3,3-Diphenylpropylamino)-1-methyl-1,4,5,6-tetrahydropyrimidine.
j) 2-(2,2-Diphenylethylamino)-1,4,5,6,7-pentahydro-1,3-diazepine.
k) 2-(3,3-Diphenylpropylamino)-1,4,5,6,7-pentahydro-1,3-diazepine.
l) 2-(2,2-Diphenylethylamino)-1,4,5,6,7,8-hexahydro-1,3-diazocine.
m) 2-(3,3-Diphenylpropylamino)-1,4,5,6,7,8-hexahydro-1,3-diazocine.
n) 2-[3,3-Bis-(4-fluorophenyl)propylamino]-1,4,5,6,7,8-hexahydro-1,3-diazocine.
o) 2-(2,2-Diphenylethylamino)-trans-3a,4,5,6,7,7a-hexahydro-1H-benzimidazole.
p) 2-(3,3-Diphenylpropylamino)-trans-3a,4,5,6,7,7a-hexahydro-1H-benzimidazole.
q) 3-(2,2-Diphenylethylamino)-2,5-dihydro-1H-2,4-benzodiazepine.
r) 3-(3,3-Diphenylpropylamino)-2,5-dihydro-1H-2,4-benzodiazepine.
s) 2-[3,3-Di(4-fluorophenyl)propylamino]-1,4,5,6-tetrahydropyrimidine hydrochloride.
t) 2-(4,4-Diphenylbutylamino)-1,4,5,6-tetrahydropyrimidine hydrochloride.
u) 2-[4,4-Di(4-fluorophenyl)butylamino]-1,4,5,6-tetrahydropyrimidine hydrochloride.
v) 2-(4,4-Diphenylbutylamino)-1,4,5,6,7,8-hexahydro-1,3-diazocine hydrochloride.
w) 2-[3,3-Di(4-fluorophenyl)propylamino]-1,4,5,6,7,8-hexahydro-1,3-diazocine hydrochloride.
x) 2-[4,4-Di(4-fluorophenyl)butylamino]-1,4,5,6,7,8-hexahydro-1,3-diazocine hydrochloride.
y) 2-(2,2-Diphenylethylamino)-1,4,5,6,7,8,9-heptahydro-1,3-diazonine hydrochloride.
z) 2-(3,3-Diphenylpropylamino)-1,4,5,6,7,8,9-heptahydro-1,3-diazonine hydrochloride.
aa) 2-(2,2-Diphenylethylamino)-1,4,5,6,7,8,9,10-octahydro-1,3-diazecine hydrochloride.
bb) 2-(3,3-Diphenylpropylamino)-1,4,5,6,7,8,9,10-octahydro-1,3-diazecine hydrochloride.
cc) 2-(2,2-Diphenylethylamino)-1,3-diazacycloundec-1-ene hydrochloride.
dd) 2-(3,3-Diphenylpropylamino)-1,3-diazacycloundec-1-ene hydrochloride.
ee) 2-(2,2-Diphenylethylamino)-1,3-diazacycloundec-1-ene hydrochloride.
ff) 2-(3,3-Diphenylpropylamino)-1,3-diazacycloundec-1-ene hydrochloride.
gg) 2-(2,2-Diphenylethylamino)-1,3-diazacyclotridec-1-ene hydrochloride.
hh) 2-(3,3-Diphenylpropylamino)-1,3-diazacyclotridec-1-ene hydrochloride.
ii) 2-[3,3-Di(4-fluorophenyl)propylamino]-1,3-diazacyclotridec-1-ene hydrochloride.
jj) 2-[4,4-Di(4-fluorophenyl)butylamino]-1,3-diazacyclotridec-1-ene hydrochloride.
kk) 2-[4-(Diphenylmethyl)-1-piperidinyl]-1,4,5,6-tetrahydropyrimidine hydrochloride.
ll) 2-[4-[Bis(4-fluorophenyl)methyl]-1-piperidinyl]-1,4,5,6-tetrahydropyrimidine hydrochloride.
mm) 2-[4-(Diphenylmethyl)-1-piperidinyl]-1,4,5,6,7,8-hexahydro-1,3-diazocine hydrochloride.
nn) 2-[4-[Bis(4-fluorophenyl)methyl]-1-piperidinyl]-1,4,5,6,7,8-hexahydro-1,3-diazocine hydrochloride.

Representative members of known cyclic guanidines for which a new use has been discovered include:
a) 2-(1,1-Diphenylmethylamino)imidazoline.
b) 2-(2,2-Diphenylethylamino)-1-methylimidazoline.

The preferred compounds of Formula I include those in which Q is represented by $(CH_2)_2$, $(CH_2)_3$, $(CH_2)_5$ or

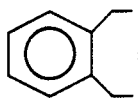

A is represented by NH—CH₂, NH—(CH₂)₂ or NH—(CH₂)₃; and both R and R₁ are represented by hydrogen. These preferred compounds are represented by Formulas II and IIa:

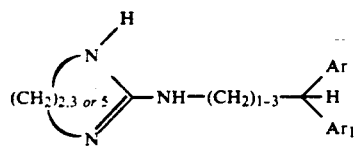

FORMULA II

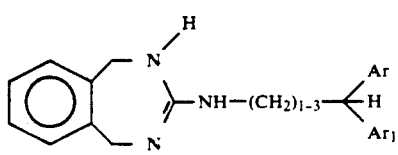

FORMULA IIa

The compounds of Formula I can be synthesized using techniques known in the art. One such technique is illustrated below.

A displacement reaction is conducted between a 2-methylthio-1,3-diazacycloalkane as described by Formula III and a diarylalkylamine as described by Formula IV below:

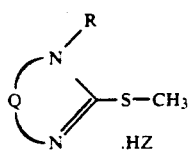

FORMULA III

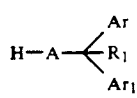

FORMULA IV

In Formula III, Q and R are as defined in Formula I. In Formula IV, R₁, A, Ar and Ar₁ are also as defined in Formula I. The 2-methylthio-1,3-diazacycloalkane of Formula III is typically present as an acid addition salt. Thus Z can be represented by any suitable anion such as, for example, I—, Br—, Cl—, CF₃SO₃—, or CH₃SO₃—. Typically, Z is represented by I—.

As is apparent to those skilled in the art, it is preferred that the non-reacting substituents appearing in both the 2-methylthio-1,3-diazacycloalkane of Formula III and the diarylalkylamine of Formula IV correspond to those appearing in the final product.

For example if the desired cyclic guanidine is 2-(2,2-diphenylethylamino)-1,4,5,6-tetrahydropyrimidine, it can be produced by conducting a displacement reaction between an acid addition salt of 2-methythio-1,4,5,6-tetrahydro-pyrimidine and 2,2-diphenylethylamine.

The displacement reaction is typically conducted at a temperature range of from about 100° C. to about 170° C., for a period of time ranging from about 10 minutes to about 90 minutes. The reaction is typically conducted neat. It can be conducted in an organic solvent such as, for example, ethanol or isopropanol. Generally, approximately equimolar quantities of the 2-methylthio-1,3-diazacyclo-alkane of Formula III and the diarylalkylamine of Formula IV are reacted together. A slight molar excess of either reactant is not deleterious to the reaction.

The cyclic guanidines of Formula I can be recovered from the reaction zone and purified by techniques well known in the art. Typically the product of the displacement reaction is dissolved in an alcohol such as methanol or isopropanol. The solution produced thereby is concentrated in order to produce a solid. This resulting solid is then redissolved in a solvent such as methanol or dichloromethane and neutralized with a base such as aqueous sodium hydroxide, thereby producing the free base of the cyclic guanidine.

The cyclic guanidine can then be recovered by forming its hydrochloride acid addition salt and then causing the precipitation of this hydrochloride salt. The hydrochloride acid addition salt of the cyclic guanidine can be formed by contacting the neutralized solution obtained above with a methanolic solution of HCl. The hydrochloride salt of the cyclic guanidine can be precipitated from solution by a variety of techniques known in the art such as conducting an azeotropic distillation in the presence of 2-butanone or isopropanol. Typically the precipitate is collected by filtration and is then further purified by recrystallization from a solvent such as isopropanol or methanol/2-butanone. Other suitable solvents for this recrystallization will be apparent to those skilled in the art. Optionally further chromatographic purification techniques can be conducted.

The diarylalkylamines of Formula IV are known in the art as are their methods of preparation.

The 2-methylthio-1,3-diazacycloalkanes of Formula III can be made by techniques well known in the art. One such technique comprises the methylation of a cyclic thiourea as described by Formula V in which Q and R are as defined in Formula I:

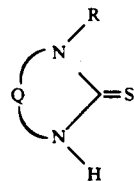

FORMULA V

As is apparent to those skilled in the art, it is preferred that the non-reacting substituents appearing in the cyclic thiourea of Formula V correspond to those appearing the 2-methylthio-1,3-diazacycloalkane of Formula III.

The methylation is typically accomplished by contacting approximately equimolar amounts of the cyclic thiourea of Formula V with methyl iodide. This methylation is typically conducted in methanol at a temperature range of from about 10° C. to about 65° C., for a period of time ranging from about 15 minutes to about 2 hours.

The acid addition salt of the 2-methylthio-1,3-diazacycloalkane produced thereby can be recovered from the reaction zone by the addition of ether and collection of the precipitated product by filtration. It can be optionally purified by recrystallization from a solvent system such as methanol/ether.

The cyclic thioureas of Formula V as well as methods for their production are well known in the art. Some are also commercially available. One method for producing these cyclic thioureas is the following reaction scheme.

Initially carbon disulfide is reacted with a diamine as described by Formula VI in which R and Q are as defined in Formula I:

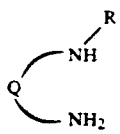

FORMULA VI

This reaction produces a dithiocarbamate inner salt as described by Formula VII in which Q and R are as defined in Formula I:

FORMULA VII

The dithiocarbamate inner salt of Formula VII is then subjected to a thermolysis reaction in order to produce the cyclic urea of Formula V.

As is apparent to those skilled in the art, the non-reacting substituents appearing in the diamine starting material of Formula VI, should correspond to those appearing in the dithiocarbamate inner salt of Formula VII.

The reaction between the diamine starting material of Formula VI and the carbon disulfide is typically conducted at a temperature range of from about 0° C. to about 20° C. for a period of time ranging from about 0.5 hours to about 3 hours. The reaction is also typically conducted in an alcoholic solvent such as ethanol. Typically the diamine and the carbon disulfide are present in the reaction medium in approximately equimolar quantities. It is not necessary to purify the dithiocarbamate inner salt produced thereby, prior to its utilization in the thermolysis reaction.

The dithiocarbamate inner salt of Formula VII is then subjected to the thermolysis reaction described above which produces the cyclic ureas of Formula V. This thermolysis reaction can be conducted either neat or in a solvent such as water. The reaction is typically conducted neat. The thermolysis is accomplished by heating the dithiocarbamate to a temperature range of about 100° C. to about 200° C. and more preferably about 130° C. to 160° C., for a period of time ranging from about 10 minutes to about 60 minutes.

The cyclic thiourea of Formula V produced by the thermolysis reaction can be recovered and purified by techniques known in the art. One suitable recovery technique is extraction with an organic solvent subsequent to the addition of water to the reaction zone. The organic layer obtained thereby is typically concentrated and the resulting concentrate is subjected to recrystallization from a solvent such as ethanol.

Alternatively, the cyclic guanidines of Formula I can be synthesized by conducting a displacement reaction between the previously described diarylalkylamine of Formula IV and a 1,3-diazacycloalkane as described by Formula VIII in which Q and R are as described in Formula I and X is represented by either Cl or OCH₃:

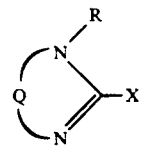

FORMULA VIII

This displacement reaction may be conducted analogously to the displacement reaction between the methylthio-1,3-diazacycloalkane of Formula III and the diarylalkylamine of Formula IV which was discussed above. The recovery and purification utilized with this alternative displacement reaction is not conducted in the same manner. Rather it is modified in the following manner.

When the displacement reaction is conducted with a 1,3-diazacycloalkane of Formula VIII in which X is represented by OCH₃, the cyclic guanidine produced thereby is present as its free base. Thus the recovery and purification scheme taught in the previous displacement reaction is modified by the omission of the neutralization step. After dissolving the reaction product in an alcohol such as methanol, the hydrochloride acid addition salt of the cyclic guanidine is formed and precipitated from solution in the manner taught previously. The precipitate is collected and further purified by recrystallization in the manner taught above.

When the displacement reaction is conducted with a 1,3-diazacycloalkane of Formula VIII in which X is represented by Cl, the compounds are recovered and purified in the following manner. This displacement reaction produces the cyclic guanidine as its hydrochloride acid addition salt. Thus the reaction product is dissolved in an alcohol and the hydrochloride salt of the guanidine is precipitated from solution in the manner taught above. The precipitate is collected and further purified by recrystallization in the manner taught above.

The 1,3-diazacycloalkanes of Formula VIII are produced in the following manner. Initially a hydroxylamine as described by Formula IX in which Q and R are as defined in Formula I is subjected to a Lossen rearrangement:

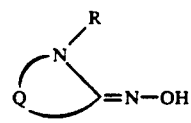

FORMULA IX

The Lossen rearrangement produces a cyclic urea as described by Formula X in which Q and R are also as defined above:

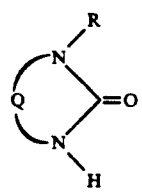

FORMULA X

The Lossen rearrangement is accomplished according to techniques known in the art. Typically the hydroxylamine is contacted with an excess of polyphosphoric acid for a period of time ranging from about 10 minutes to about 3 hours. The rearrangement is typically conducted at a temperature range of from about 100° C. to about 200° C.

The cyclic urea of Formula X produced thereby is recovered and purified according to techniques known in the art. It is typically recovered by extraction with an organic solvent. The resulting organic layer is typically concentrated and subjected to recrystallization in a solvent such as ethanol.

The 1,3-diazacycloalkanes of Formula VIII in which X is represented by $OCH_3$ can be obtained from a cyclic urea of Formula X in the following manner. A cyclic urea of Formula X is contacted with an equimolar quantity of dimethylsulfate, $(CH_3)_2SO_4$. The reaction is typically conducted at a temperature range of from about 0° C. to about 100° C. for a period of time ranging from about 2 hours to about 14 hours.

The 1,3-diazacycloalkanes of Formula VIII in which X is represented by Cl can be obtained by contacting a cyclic urea of Formula X with about an equimolar quantity of phosphorus oxychloride, $(POCl_3)$. The reaction is typically conducted at a temperature range of from about 20° C to about 100° C. for a period of time ranging from about 2 hours to about 14 hours.

The 1,3-diazacycloalkanes of Formula VIII can be recovered and purified by techniques known in the art. They can be recovered by extraction with an organic solvent after water has been added to the reaction zone. The resulting organic layer is typically concentrated and the resulting concentrate is recrystallized from a solvent system such as ethyl acetate/hexane.

The cyclic thioureas previously described by Formula V in which Q and R are as defined in Formula I can also be produced from the cyclic urea of Formula X.

FORMULA V

This is accomplished by reacting the cyclic urea of Formula X with a thionating agent such as Lawesson's Reagent for a period of time ranging from about 0.5 hours to about 14 hours. The reaction is typically conducted at a temperature range of from about 20° C. to about 110° C. in a solvent such as tetrahydrofuran or toluene. Once the cyclic thiourea of Formula V is formed, it can be recovered and purified by the method previously taught above. It can then be utilized to form the 2-methylthio-1,3-diazacycloalkane of Formula III in the manner taught above.

As noted above, the compounds of Formula I are calcium antagonists.

One method of demonstrating that the compounds of Formula I are effective as calcium antagonists is the following test protocol. The protocol is based upon the fact that calcium ions increase the force of contraction of smooth muscle fibers. Thus, the compounds are introduced into a tissue bath containing both smooth muscle fibers and calcium ions, and the effect the compounds have upon the force of contraction of the muscle fibers is measured.

The test is conducted in the following manner. Pieces of ileum, 2 cm in length, from male guinea pigs (200–400 g) are set up in isolated organ baths in $Ca^{++}$-free $K^+$ Tyrode's solution (in mM, NaCl 137, KCl 40, $NaH_2PO_4$ 0.4, $NaHCO_3$ 11.9, glucose 5.5) and gassed with 95% $O_2$, 5% $CO_2$ at 37° C. Contractions are obtained by adding calcium chloride into the bath, and measured isotonically with a 1 g load. Cumulative dose-response curves of calcium chloride are obtained. Tissues are then washed and incubated with the test compounds for 20-25 minutes and then $Ca^{++}$ concentration response curves re-established. The preparations are stable for at least 5 hours and give reproducible dose-response curves to $Ca^{++}$. Dose ratios are determined graphically at $ED_{50}$ values from the $Ca^{++}$ dose-response curve and Schild plots are constructed to determine $pA_2$ value using inverse regression line analysis; O. Arunlakshana and H.O. Schild, Brit. J. Pharmacol. 14: 48-52, 1959. Alternatively, when only one concentration of an antagonist is used, $pA_2$ values can be calculated according to the method of J. M. Van Rossum, Arch. Int. Pharmacodyn Ther. 143: 299-330, 1963.

Since the compounds of Formula I are calcium antagonists, they are effective in the treatment of a number of disease states. They are useful in the treatment of angina, hypertension, mania, epilepsy, depression, primary pulmonary hypertension, hyperurecemia, achalasia, asthma, Raynaud's phenomenon, and cardiac arrhythmias. The compounds also exhibit vasodilatory properties and thus are useful where such a physiological effect is desirable, such as, for example, in the treatment of congestive heart failure.

It has been recently reported that excessive levels of intracellular calcium ions in ischemic tissue have been associated with an increased incidence of cellular death and damage, when those ischemic tissues are reperfused as the result of treatment with thrombolytic agents such as TPA or streptokinase. This phenomenon has been referred to as calcium overload. The compounds of Formula I are effective in the treatment of calcium overload.

These conditions and diseases discussed above can be relieved by administering to a patient in need thereof, a compound of Formula I in an amount sufficient to treat the disease or condition (i.e. an antihypertensive amount, antianginal amount, antimanic amount, etc.). This quantity will be within the dosage range at which the compounds exhibit their calcium antagonistic effects.

The dosage range at which these compounds produce their calcium antagonist effects can vary widely depending upon the particular compound being administered, the particular disease or condition being treated as well as its severity, the patient, other underlying disease states the patient is suffering from, the route of administration, and other medications that may be concurrently administered to the patient. Generally the compounds will exhibit their calcium antagonistic properties at a dosage range of from 0.01 mg/kg of patient body weight/day to about 100 mg/kg of patient body weight/day.

The compounds of the present invention may be administered by a variety of routes. They are effective if administered orally. The compounds may also be administered parenterally (i.e. subcutaneously, intravenously, intramuscularly, or intraperitoneally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tabletted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compounds may also be incorporated into any inert carrier so that they may be utilized in routine serum assays, blood levels, urine levels, etc. according to techniques well known in the art.

As used in this application:

a) the term "patient" refers to a warm-blooded animal, such as, for example, rats, mice, dogs, cats, guinea pigs, and primates such as humans.

b) the terms "treat" and "treatment" refers to either relieving or alleviating the patient's disease or condition.

c) the term "angina" refers to either variant angina or exertional angina as those terms are defined in the Seventh Edition of Goodman and Gilman's, The Pharmacological Basis of Therapeutics.

d) the terms "epilepsy, mania, hypertension, depression, achalasia, asthma, and congestive heart failure" are used in the manner defined in the Thirteenth Edition of the Merck Manual.

e) the term "vasodilatory" is used in the manner defined in the 27th Edition of Dorland's Illustrated Medical Dictionary.

f) the term "arrhythmia" refers to any variation from the normal rhythm of the heart beat.

g) the term "primary pulmonary hypertension" refers to a condition in which there is elevated arterial pressures in the small pulmonary arteries.

The following examples are presented in order to further illustrate the present invention. They should not be construed as limiting the claimed scope in any manner.

EXAMPLE 1

The purpose of this example is to demonstrate the preparation of a known cyclic guanidine, 2-(1,1-diphenylmethylamino)imidazoline.

A flask containing a mixture of 2-methylthioimidazoline hydroiodide (7.40 g, $3.00 \times 10^{-2}$ mole) and 1,1-diphenylmethylamine (5.50 g. $3.00 \times 10^{-2}$ mole) was immersed in an oil bath which had been preheated to ca. 155° C. The mixture was stirred at between 150°-160° C. for 30 minutes. The resulting yellow glass was dissolved in minimal methanol. 2-Butanone was added and the solution was concentrated. After being allowed to stand in the freezer for several days, 5.70 g (50%) of the product hydroiodide was collected by filtration. This was dissolved in methanol (32 ml) and the solution was basified by the addition of 2N NaOH (16 ml, $3.2 \times 10^{-2}$ mole). The resulting precipitate was collected by filtration yielding 3.19 g (42%) of the free base. This was dissolved in methanol (50 ml) and the resulting solution was cooled to 0° C. at which time a methanolic solution of HCl was added. After 5–10 minutes the methanol was evaporated and isopropanol was added. The product crystallized and was collected by filtration. Recrystallization from isopropanol afforded 2-(1,1-diphenylmethylamino)imidazoline hydrochloride as tiny colorless needles: 2.64 g (31%), m.p. 210–212° C. (lit. m.p. 207–209° C.).

Anal. Calcd, for $C_{16}H_{17}N_3 \cdot HCl$: C, 66.78; H, 6.30; N, 14.60. Found: C, 66.59, H, 6.24, N, 14.67.

EXAMPLE 2

The purpose of this example is to demonstrate the preparation of one of the known cyclic guanidines, 2-(2,2-diphenylethylamino)-1-methylimidazoline.

A flask containing a mixture of 1-methyl-2-methylthioimidazoline hydroiodide (2.58 g, $1.00 \times 10^{-2}$ mole) and 2,2diphenylethylamine (1.97 g, $1.00 \times 10^{-2}$ mole) was immersed in an oil bath which had been preheated to ca. 155° C. The mixture was stirred at between 150°-155° C. for ca. 20 minutes. The resulting yellow glass was treated with isopropanol and the solid was collected by filtration affording a colorless powder which was dissolved in methanol (20 ml). Basification by the slow addition of 2N aqueous NaOH (20 ml, $4.0 \times 10^{-2}$ mole) afforded a colorless solid which was collected by filtration. This was dissolved in methanol and the solution was cooled to 0° C. before being treated with a methanolic solution of HCl. The methanol was evaporated and the resulting solid was crystallized from isopropanol affording 2-(2,2-diphenylethylamino)-1-methylimidazoline hydrochloride as off-white crystals: 2.15 g (83%), m.p. 238°-241° C. (decomp). (Lit. m.p. 235°-237° C.).

Anal Calcd. for $C_{18}H_{21}N_3 \cdot HCl$: C, 68.45; H, 7.02; N, 13.30. Found: C, 68.35; H, 7.19; N, 13.29.

EXAMPLE 3

The purpose of this example is to demonstrate the preparation of one member of the new class of cyclic guanidines as described by Formula I, 2-(2,2-diphenylethylamino)imidazoline.

A flask containing a mixture of 2-methylthioimidazoline hydroiodide (3.66 g, $1.50 \times 10^{-2}$ mole) and 2,2-diphenylethylamine (2.96 g, $1.50 \times 10^{-2}$ mole) was immersed in an oil bath which had been preheated to ca. 155° C. The mixture was stirred at between 150°-160° C. for 30 minutes. The resulting yellow glass was dissolved in methanol. Evaporation of the methanol gave a yellow oil which was dissolved in ethyl acetate. The solution was transferred to a separatory funnel where it was washed with 2N NaOH and saturated aqueous NaCl. After being dried over anhydrous $Na_2SO_4$, the solution was treated with a methanolic solution of HCl. The solvent was evaporated leaving a foam which was dissolved in a minimum amount of methanol 2-Butanone was added and the solution was concentrated. After being allowed to stand in the freezer for several days, the product was collected by filtration. Recrystallization from isopropanol afforded 2-(2,2-diphenylethylamino)imidazolinehydrochloride as a colorless solid: 1.97 g (44%), m.p. 162°–164° C.

Anal. Calcd. for $C_{17}H_{19}N_3 \cdot HCl$: C, 67.65; H, 6.68, N, 13.92. Found: C, 67.54; H, 6.71; N, 13.80.

EXAMPLE 4

The purposes of this example is to demonstrate the preparation of one member of the new class of cyclic guanidines as described by Formula I, 2-(3,3-diphenylpropylamino)imidazoline.

To a refluxing solution of 2-methylthioimidazoline hydroiodide (3.66 g, $1.50 \times 10^{-2}$ mole) and isopropanol (20 ml) was added a solution of 3,3-diphenylpropylamine (3.17 g $1.50 \times 10^{-2}$ mole) and isopropanol (10 ml). After being refluxed for ca. 24 hours, heating was discontinued and the reaction was allowed to cool to room temperature. After two days, the precipitate was collected by filtration affording the guanidine hydroiodide was a colorless powder. The hydroiodide was stirred for ca. 17 hours in a two phase mixture of dichloromethane (63 ml) and 5M aqueous NaOH (69 ml). The dichloromethane layer was separated and washed with saturated aqueous NaCl. After being dried over anhydrous $Na_2SO_4$, the dichloromethane was evaporated leaving a colorless foam which was dissolved in methanol (48 ml). The methanolic solution was cooled to 0° C. before being treated with a methanolic solution of HCl. After 30 minutes, the methanol was evaporated and the resulting foam was slurried with ethyl acetate for ca. 17 hours. The resulting solid was collected by filtration affording an off white powder which was crystallized from methanol/2-butanone giving 2-(3,3-diphenylpropylamino)imidazoline hydrochloride as colorless crystals: 1.61 g (50%), m.p. 119°–120° C.

Anal Calcd. for $C_{18}H_{21}N_3 \cdot HCl$: C, 68.45; H, 7.02; N, 13.30. Found: C, 68.14; H, 7.14; N, 13.17.

EXAMPLE 5

The purpose of this example is to demonstrate the preparation of one member of the new class of cyclic guanidines as described by Formula I, 2-(3,3-diphenylpropylamino)-1-methylimidazoline.

A flask containing a mixture of 3,3-diphenylpropylamine (2.11 g, $1.00 \times 10^{-2}$ mole) and 1-methyl-2-methylthioimidazoline hydroiodide (2.58 g, $1.00 \times 10^{-2}$ mole) as immersed in an oil bath which had been preheated to ca. 155° C. The mixture was stirred at between 150°–160° C. for ca. 30 minutes. The resulting yellow glass was dissolved in methanol. Evaporation of most of the methanol and addition of isopropanol afforded a colorless solid which was collected by filtration. This was dissolved in methanol (20 ml) and the solution was basified by the addition of 2N aqueous NaOH (20 ml, $4.0 \times 10^{-2}$ mole). The resulting colorless solid was collected by filtration and dried by suction. The free base was dissolved in methanol (35 ml) and the solution was cooled to 0° C. after being treated with a methanolic solution of HCl. After ca. 15–20 minutes the methanol was evaporated. Addition of isopropanol gave a colorless solid which was collected by filtration. Crystallization from isopropanol afforded 2-(3,3-diphenylpropylamino)-1-methylimidazoline hydrochloride as an off-white solid: 2.00 g (74%), m.p. 202°–204° C.

Anal. Calcd. for $C_{19}H_{23}N_3 \cdot HCl$: C, 69.18; H, 7.33; N, 12.74. Found: C, 69.11; H, 7.41; N, 12.72.

EXAMPLE 6

The purpose of this example is to demonstrate the preparation of one member of the new class of cyclic guanidines as described by Formula I, 2-(2,2-diphenylethylamino)-1,4,5,6-tetrahydropyrimidine.

A flask containing a mixture of 2,2-diphenylethylamine (5.92 g; $3.00 \times 10^{-2}$ mole) and 2-methylthio-1,4,5,6-tetrahydropyrimidine hydroiodide (7.74 g, $3.00 \times 10^{-2}$ mole) was immersed in an oil bath which had been preheated to ca. 155° C. The reaction was stirred at between 150°–168° C. for 1.5 hours. The resulting yellow glass was dissolved in methanol. The methanol was evaporated and the resulting yellow oil was dissolved in dichloromethane. This solution was transferred to a separatory funnel where it was washed with 2N aqueous NaOH and saturated aqueous NaCl. After drying over anhydrous $Na_2SO_4$, the dichloromethane was evaporated giving a foam which was dissolved in methanol (125 ml). This solution was cooled to 0° C. at which time it was treated with a methanolic solution of HCl. After 10–15 minutes most of the methanol was evaporated and 2-butanone was added. After several days the crystals were collected by filtration. Recrystallization from isopropanol afforded 2-(2,2-diphenylethylamino)-1,4,5,6-tetrahydropyrimidine hydrochloride as off-white crystals: 3.80 g (40%), m.p. 180°–182° C.

Anal. Calcd. for $C_{18}H_{21}N_3 \cdot HCl$: C, 68.45; H, 7.02; N, 13.30. Found: C, 68.17; H, 7.02; N, 13.16.

EXAMPLE 7

The purpose of this example is to demonstrate the preparation of one member of the new class of cyclic guanidines as described by Formula I, 2-(3,3-diphenylpropylamino)-1-methyl-1,4,5,6-tetrahydropyrimidine.

A flask containing 1-methyl-2-methylthio-1,4,5,6-tetrahydropyrimidine hydroiodide (6.00 g, $2.20 \times 10^{-2}$ mole) and 3,3-diphenylpropylamine (4.91 g, $2.32 \times 10^{-2}$ mole) was immersed in an oil bath which had been preheated to ca. 155° C. The reaction was stirred at between 150°–165° C. for 50 minutes. The resulting yellow glass was dissolved in methanol. The methanol was partially evaporated at reduced pressure and isopropanol was added. The evaporation was continued being stopped periodically for the addition of small portions of isopropanol. A solid formed which was subsequently collected by filtration. This material was dissolved in a two phase mixture of 5 molar aqueous NaOH (100 ml) and $CH_2Cl_2$ (100 ml). After stirring overnight, the $CH_2Cl_2$ layer was separated. The aqueous alkaline layer was extracted with $CH_2Cl_2$ ($2\times$). The $CH_2Cl_2$ layers were combined, washed with $H_2O$ ($2\times$), washed with saturated aqueous NaCl, and dried over anhydrous $Na_2SO_4$. The drying agent was removed by filtration and the filtrate was evaporated at reduced pressure leaving a colorless foam which was dissolved in methanol (50 ml). The solution was cooled to 0° C. before being treated with a methanolic solution of HCl. The methanol was partially evaporated at reduced pressure. 2-Butanone was added and the evaporation was continued on the steam bath until the temperature of the solution reached 78°–79° C. After cooling to room temperature, the solution deposited a solid which was collected by filtration. The product was recrystallized from methanol/2-butanone affording 2-(3,3-diphenylpropylamino)-1-methyl-1,4,5,6-tetrahydropyrimidine hydroiodide as a colorless solid: 3.44 g (45%), m.p. 178°–180° C.

Anal. Calcd. for $C_{20}H_{25}N_3 \cdot HCl$: C, 69.85; H, 7.62; N, 12.22. Found: C, 69.63; H, 7.68; N, 12.19.

EXAMPLE 8

The purpose of this example is to demonstrate the preparation of one member of the new class of cyclic guanidines as described by Formula I, 2-(2,2-diphenylethylamino)-1,4,5,6,7-pentahydro-1,3-diazepine.

A flask containing 2-methylthio-1,4,5,6,7-pentahydro-1,3-diazepine hydroiodide (5.44 g, $2.00 \times 10^{-2}$ mole) was 2,2-diphenylethylamine (3.94 g, $2.00 \times 10^{-2}$ mole) was immersed in an oil bath which had been preheated to ca. 155° C. The reaction was stirred at between 150°–155° C. for 1.5 hours. The resulting yellow glass was dissolved in methanol. The methanol was partially evaporated and isopropanol was added. The evaporation was continued, being stopped periodically for the addition of small portions of isopropanol. A precipitate formed and this was collected by filtration. This material was dissolved in a two phase mixture of 5 molar aqueous NaOH (100 ml) and $CH_2Cl_2$ (100 ml). After stirring overnight, the $CH_2Cl_2$ layer was separated. The aqueous alkaline layer was extracted with $CH_2Cl_2$ (2×). The $CH_2Cl_2$ layers were combined, washed with $H_2O$, washed with saturated aqueous NaCl, and dried over anhydrous $Na_2SO_4$. The drying agent was removed by filtration and the filtrate was evaporated at reduced pressure leaving a colorless foam which was dissolved in methanol (55 ml). The solution was cooled to 0° C. before being treated with a methanolic solution of HCl. The methanol was evaporated at reduced pressure yielding an oil which slowly crystallized. The product was triturated with a mixture of isopropanol and 2-butanone before being collected by filtration. Crystallization from isopropanol afforded 2-(2,2-diphenylethylamino)-1,4,5,6,7-pentahydro-1,3-diazepine hydrochloride as a colorless solid: 3.75 g (57%), m.p. 173°–175° C.

Anal. Calcd. for $C_{19}H_{23}N_3 \cdot HCl$: C, 69.18; H, 7.33; N, 12.74. Found: C, 68.95; H, 7.44; N, 12.69.

EXAMPLE 9

The purpose of this example is to demonstrate the preparation of one member of the new class of cyclic guanidines as described by Formula I, 2-(2,2-diphenylethylamino)-1,4,5,6,7,8-hexahydro-1,3-diazocine.

A flask containing 2-methylthio-1,4,5,6,7,8-hexahydro-1,3-diazocine hydroiodide (3.00 g, $1.05 \times 10^{-2}$ mole) and 2,2-diphenylethylamine (2.08 g, $1.05 \times 10^{-2}$ mole) was immersed in an oil bath which had been preheated to ca. 155° C. The reaction was stirred at between 150°–160° C. for ca. 1 hour. The resulting yellow glass was dissolved in methanol. The methanol was evaporated leaving a foam which was dissolved in a two phase mixture of 5 molar aqueous NaOH (65 ml) and $CH_2Cl_2$ (60 ml). After stirring overnight the $CH_2Cl_2$ layer was separated. The aqueous alkaline layer was extracted with $CH_2Cl_2$ (2×). The $CH_2Cl_2$ layers were combined, washed with $H_2O$ (2×), washed with saturated aqueous NaCl, and dried over anhydrous $Na_2SO_4$. The drying agent was removed by filtration and the filtrate was evaporated at reduced pressure leaving a foam. The foam was dissolved in methanol (15 ml) and the solution was cooled to 0° C. This solution was then treated with a methanolic solution of HCl. The solution was treated with charcoal which was sub- sequently removed by filtration through a pad of celite. The filtrate was concentrated on the steam bath and 2-butanone was added periodically until the temperature of the solution reached ca. 80° C. Upon cooling the solution deposited a solid which was collected by filtration. This material was recrystallized two times from methanol/2-butanone affording 2-(2,2-diphenylethylamino)-1,4,5,6,7,8-hexahydro-1,3-diazocine hydrochloride as an off-white solid: 0.80 g (22%), m.p. 195°–197° C.

Anal. Calcd. for $C_{20}H_{25}N_3 \cdot HCl$: C, 69.85; H, 7.62; N, 12.22. Found: C, 69.74; H, 7.74; N, 12.21.

EXAMPLE 10

The purpose of this example is to demonstrate the preparation of one member of the new class of cyclic guanidines as described by Formula I, 2-(3,3-diphenylpropylamino)-1,4,5,6,7,8-hexahydro-1,3-diazocine.

A flask containing 2-methylthio-1,4,5,6,7,8-hexahydro-3-diazocine hydroiodide (2.82 g, $9.86 \times 10^{-3}$ mole) and 3,3-diphenylpropylamine (2.09 g, $9.86 \times 10^{-3}$ mole) was immersed in an oil bath which had been preheated to ca. 155° C. The reaction was stirred at between 150°–160° C. for ca. 1 hour. The resulting yellow glass was dissolved in methanol. The methanol was subsequently evaporated at reduced pressure and the concentrate was dissolved in a two phase mixture of 5 molar aqueous NaOH (66 ml) and $CH_2Cl_2$ (62 ml). After stirring overnight the $CH_2Cl_2$ layer was separated. The aqueous alkaline layer was extracted with $CH_2Cl_2$ (2×). The $CH_2Cl_2$ layers were combined, washed with $H_2O$ (2×), washed with saturated aqueous NaCl, and dried over anhydrous $Na_2SO_4$. The drying agent was removed by filtration and the filtrate was evaporated at reduced pressure leaving a yellow foam. This was dissolved in methanol (45 ml) and the solution was cooled to 0° C. This solution was then treated with a methanolic solution of HCl. The solution was treated with charcoal which was then removed by filtration through a pad of celite. The filtrate was evaporated on the steam bath and 2-butanone was periodically added until the temperature of the solution reached ca. 80° C. Upon cooling the solution deposited a solid which was collected by filtration. This material was recrystallized two times from methanol/2-butanone affording 2-(3,3-diphenylpropylamino)-1,4,5,6,7,8-hexahydro-1,3-diazocine hydrochloride as an off-white solid: 0.58 g (16%), m.p. 160°–162° C.

Anal. Calcd. for $C_{21}H_{27}N_3 \cdot HCl$: C, 70.47; H, 7.88; N, 11.74. Found: C, 70.27; H, 8.01; N, 11.58.

EXAMPLE 11

The purpose of this example is to demonstrate the preparation of one member of the new class of cyclic guanidines as described by Formula I, 2-(3,3-diphenylpropylamino)-1,4,5,6,7-pentahydro-1,3-diazepine.

A flask containing 2-methylthio-1,4,5,6,7-pentahydro-1,3-diazepine hydroiodide (2.72, $1.00 \times 10^{-2}$ mole) and 3,3-diphenylpropylamine (2.11 g, $1.00 \times 10^{-2}$ mole) was immersed in an oil bath which had been preheated to ca. 155° C. The reaction was stirred at between 155°–160° C. for ca. 1.5 hours. The resulting yellow glass was dissolved in methanol. The methanol was evaporated at reduced pressure leaving a foam which was dissolved in a two phase mixture of 5 molar aqueous NaOH (57 ml) and $CH_2Cl_2$ (53 ml). After stirring overnight the $CH_2Cl_2$ layer was separated. The aqueous alkaline layer was extracted with $CH_2Cl_2$ (2×). The CH$_2$Cl$_2$ layers were combined, washed with H$_2$O (2×), washed with saturated aqueous NaCl, and dried over anhydrous Na$_2$SO$_4$. The drying agent was removed by filtration and the filtrate was evaporated at reduced pressure leaving a foam which was dissolved in methanol (39 ml). This solution was cooled to 0° C. before being treated with a methanolic solution of HCl. The solution was treated with charcoal which was subsequently removed by filtration through a pad of celite. The filtrate was concentrated on the steam bath and 2-butanone was added periodically until the temperature of the solution approached 80° C. Upon cooling the solution deposited a solid which was collected by filtration. This material was recrystallized from methanol/2-butanone affording 2-(3,3-diphenylpropylamino)-1,4,5,6,7-pentahydro-1,3-diazepine hydrochloride as an off-white solid: 1.78 g (52%), m.p. 151°-152° C.

Anal. Calcd. for C$_{20}$H$_{25}$N$_3$.HCl: C, 69.85; H, 7.62; N, 12.22. Found: C, 69.73; H, 7.72; N, 12.14.

EXAMPLE 12

The purpose of this example is to demonstrate the preparation of one member of the new class of cyclic guanidines as described by Formula I, 2-(2,2-diphenylethylamino)-1-methyl-1,4,5,6-tetrahydropyrimidine.

A flask containing 1-methyl-2-methylthio-1,4,5,6-tetrahydropyrimidine hydroiodide (9.80 g, 3.60×10$^{-2}$ mole) and 2,2-diphenylethylamine (7.49 g, 3.80×10$^{-2}$ mole) was immersed in an oil bath which had been preheated to ca. 155° C. The reaction was stirred at between 150°-170° C. for 45 minutes. The resulting yellow glass was dissolved in methanol. Most of the methanol was evaporated at reduced pressure and isopropanol was added. The evaporation was continued, being stopped periodically for the addition of small portions of isopropanol. A solid forms which was collected by filtration affording a colorless solid. This was dissolved in a two phase mixture of 50% aqueous NaOH (60 ml) and CH$_2$Cl$_2$ (100 ml). After stirring overnight, the CH$_2$Cl$_2$ layer was separated. The aqueous alkaline layer was extracted with CH$_2$Cl$_2$ (2×). The CH$_2$Cl$_2$ layers were combined, washed with H$_2$O (2×), washed with saturated aqueous NaCl, and dried over anhydrous Na$_2$SO$_4$. The drying agent was removed by filtration and the filtrate was evaporated at reduced pressure leaving a foam which was dissolved in methanol (40 ml). This solution was cooled to 0° C. before being treated with a methanolic solution of HCl. The methanol was partially evaporated and isopropanol was added. The evaporation was continued, being stopped periodically for the addition of small portions of isopropanol. A solid formed and the flask was placed in the refrigerator. After several hours, the product was collected by filtration. Crystallization from isopropanol afforded 2-(2,2-diphenylethylamino)-1-methyl-1,4,5,6-tetrahydropyrimidine hydrochloride as a colorless solid: 2.66 g (22%), m.p. 155°-157° C.

Anal. Calcd. for C$_{19}$H$_{23}$N$_3$.HCl: C, 69.18; H, 7.33; N, 12.74. Found: C, 69.11; H, 7.35; N, 12.95.

EXAMPLE 13

The purpose of this example is to demonstrate the preparation of one member of the new class of cyclic guanidines as described by Formula I, 2-(3,3-diphenylpropylamino)-1,4,5,6-tetrahydropyrimidine.

A stirred mixture of 2-methylthio-1,4,5,6-tetrahydropyrimidine hydroiodide (3.87 g, 1.50×10$^{-2}$ mole) and isopropanol (20 ml) was heated to reflux. To this solution was added a solution of 3,3-diphenylpropylamine (3.17 g, 1.50×10$^{-2}$ mole) and isopropanol (10 ml). After refluxing 27 hours, the solvent was evaporated at reduced pressure. The resulting oil was slurried with ethyl acetate for two days and the resulting solid was collected by filtration. This material was dissolved in a two phase mixture of 5 molar aqueous NaOH (48 ml) and CH$_2$Cl$_2$ (44 ml). After stirring overnight, the CH$_2$Cl$_2$ layer was separated. The aqueous alkaline layer was extracted with CH$_2$Cl$_2$ (2×). The CH$_2$Cl$_2$ phases were combined, washed with H$_2$O (2×), washed with saturated aqueous NaCl, and dried over anhydrous Na$_2$SO$_4$. The drying agent was removed by filtration and the filtrate was evaporated at reduced pressure. The concentrate was dissolved in methanol (60 ml) and the resulting solution was cooled to 0° C. before being treated with a methanolic solution of HCl. The methanol was evaporated at reduced pressure and the resulting foam was slurried with ethyl acetate. After stirring overnight, a solid was collected by filtration. This material was dissolved in methanol and the solution was treated with charcoal. The charcoal was removed by filtration through a pad of celite and the filtrate was partially evaporated on the steam bath. 2-Butanone was occasionally added until the temperature of the solution reached 79°-80° C. After cooling to room temperature, the precipitate was collected by filtration. Crystallization from methanol/2-butanone afforded 2-(3,3-diphenylpropylamino)-1,4,5,6-tetrahydro-pyrimidine hydrochloride as a colorless solid: 1.44 g (29%), m.p. 144°-146° C.

Anal. Calcd. for C$_{19}$H$_{23}$N$_3$.HCl: C, 69.18; H, 7.33; N, 12.74. Found: C, 69.25; H, 7.36; N, 12.80.

EXAMPLE 14

The purpose of this example is to demonstrate the preparation of one member of the new class of cyclic guanidines as described by Formula I, 2-(4,4-diphenylbutylamino)-1-methylimidazoline.

A flask containing 1-methyl-2-methylthioimidzoline hydroiodide (2.58 g 1.00×10$^{-2}$ mole) and 4,4-diphenylbutylamine (2.25 g, 1.00×10$^{-2}$ mole) was immersed in an oil bath which had been preheated to ca. 155° C. The was heated at between 150°-160° C. for 1 hour. The resulting yellow glass was dissolved in methanol. The methanol was evaporated at reduced pressure and isopropanol was added periodically with continued concentration until the solution became turbid. After standing, a colorless solid was collected by filtration. This material was dissolved in a stirred, two phase mixture of 5 molar aqueous NaOH (56 ml) and CH$_2$Cl$_2$ (51 ml). After stirring overnight, the CH$_2$Cl$_2$ layer was separated. The aqueous alkaline layer was extracted with CH$_2$Cl$_2$ (2×). The CH$_2$Cl$_2$ layers were combined, washed with H$_2$O (2×), washed with saturated aqueous NaCl, and dried over anhydrous Na$_2$SO$_4$. The drying agent was removed by filtration and the filtrate was evaporated to a foam which was dissolved in methanol (40 ml). This solution was cooled to 0° C. before being treated with a methanolic solution of HCl. The methanol was evaporated at reduced pressure and the concentrate was crystallized two times from methanol/2-butanone affording 2-(4,4-diphenylbutylamino)-1-methylimidazoline hydrochloride as a colorless solid: 1.07 g (31%), m.p. 158°-159° C.

Anal. Calcd. for C$_{20}$H$_{25}$N$_3$.HCl: C, 69.85; H, 7.62; N, 12.22. Found: C, 69.92; H, 7.71; N, 12.26.

EXAMPLE 15

The purpose of this example is to demonstrate the preparation of one member of the new class of cyclic guanidines as described by Formula I, 2-(2,2-diphenylethylamino)-trans-3a,4,5,6,7,7a-hexahydro-1H-benzimidazole.

A flask containing 2-methylthio-trans-3a,4,5,6,7,7a-hexahydro-1H-benzimidazole hydroiodide (4.39 g, $1.47 \times 10^{-2}$ mole) and 2,2-diphenylethylamine (2.90 g, $1.47 \times 10^{-2}$ mole) was immersed in an oil bath which had been preheated to ca. 155° C. The reaction was stirred at between 155°-165° C. for 40 minutes. The resulting yellow glass was dissolved in methanol. The methanol was evaporated at reduced pressure and isopropanol was added periodically during the course of the evaporation. When the solution had been concentrated to ca. 20 ml, it was set aside to cool. After 4 days the solution had deposited a solid which was collected by filtration. This guanidine hydroiodide was dissolved in a two phase mixture of 5 molar aqueous NaOH (100 ml) and $CH_2Cl_2$ (100 ml). After stirring overnight the $CH_2Cl_2$ layer was separated. The aqueous alkaline layer was extracted with $CH_2Cl_2$ ($2\times$). The $CH_2Cl_2$ layers were combined, washed with $H_2O$ ($2\times$), washed with saturated aqueous NaCl, and dried over anhydrous $Na_2SO_4$. The drying agent was removed by filtration and the filtrate was evaporated at reduced pressure leaving a colorless foam which was dissolved in methanol (50 ml). The solution was cooled to 0° C. before being treated with a methanolic solution of HCl. The methanol was evaporated at reduced pressure leaving a foam. The foam was dissolved in methanol (10-15 ml) and 2-butanone was added. The solution was then concentrated on the steam bath. When the temperature of the solution reached ca. 75° C. a solid began to precipitate and the evaporation was stopped. After standing 2 hours the precipitate was collected by filtration affording a solid. This material was recrystallized from methanol/2-butanone affording 2-2,2-diphenylethylamino)-trans-3a,4,5,6,7,7a-hexahydro-1H-benzimidazole hydrochloride as a colorless solid: 3.86 g (74%), m.p. 216°-218° C.

Anal. Calcd. for $C_{21}H_{25}N_3 \cdot HCl$: C, 70.87; H, 7.36; N, 11.81. Found: C, 70.74; H, 7.51; N, 11.71.

EXAMPLE 16

The purpose of this example is to demonstrate the preparation of one member of the new class of cyclic guanidines as described by Formula I, 2-(3,3-diphenylpropylamino)-trans-3a,4,5,6,7,7a-hexahydro-1H-benzimidazole.

A flask containing 2-methylthio-trans-3a,4,5,6,7,7a-hexahydro-1H-benzimidazole hydroiodide (3.00 g, $1.01 \times 10^{-2}$ mole) and 3,3-diphenylpropylamine (2.13 g, $1.01 \times 10^{-2}$ mole) was immersed in an oil bath which had been preheated to ca. 155° C. The reaction was stirred at between 150°-160° C. for 1 hour. The resulting yellow glass was dissolved in methanol. The solution was treated with charcoal which was subsequently removed by filtration through a pad of celite. The filtrate was evaporated at reduced pressure affording a foam which was dissolved in a stirred, two phase mixture of 5 molar aqueous NaOH (70 ml) and $CH_2Cl_2$ (65 ml). After stirring over the weekend, the $CH_2Cl_2$ layer was separated. The aqueous alkaline layer was extracted with $CH_2Cl_2$ ($2\times$). The $CH_2Cl_2$ layers were combined, washed with $H_2O$ ($2\times$), washed with saturated aqueous NaCl, and dried over anhydrous $Na_2SO_4$. The drying agent was removed by filtration and the filtrate was evaporated at reduced pressure leaving an oil which was dissolved in methanol (43 ml). This solution was cooled to 0° C. before being treated with a methanolic solution of HCl. This solution was treated with charcoal which was subsequently removed by filtration through a pad of celite. The filtrate was evaporated on the steam bath and 2-butanone was added periodically until the temperature approached 80° C. The solution was then placed in the freezer. After ca. 3 days, a solid was collected by filtration. This material was recrystallized two times from methanol/2-butanone affording 2-(3,3-diphenylpropylamino)-trans-3a,4,5,6,7,7a-hexahydro-1H-benzimidazole hydrochloride as a colorless solid: 1.18 g (32%), m.p. 155°-157° C.

Anal. Calcd. for $C_{22}H_{27}N_3 \cdot HCl$: C, 71.43; H, 7.63; N, 11.36. Found: C, 71.50; H, 7.69; N, 11.34.

EXAMPLE 17

The purpose of this example is to demonstrate the preparation of one member of the new class of cyclic guanidines as described by Formula I, 3-(2,2-diphenylethylamino)-2,5-dihydro-1H-2,4-benzodiazepine.

A flask containing 2-methylthio-2,5-dihydro-1H-2,4-benzodiazepine hydroiodide (3.20 g $1.00 \times 10^{-2}$ mole) and 2,2-diphenylethylamine (5.91 g, $3.00 \times 10^{-2}$ mole) was immersed in an oil bath which had been preheated to ca. 155° C. The reaction was stirred at between 150°-160° C. for ca. 30 minutes. The resulting solid mass was treated with isopropanol and that which did not dissolve was collected by filtration. This guanidine hydroiodide was dissolved in a two phase mixture of 5 molar aqueous NaOH (80 ml) and $CH_2Cl_2$ (80 ml). After stirring overnight the $CH_2Cl_2$ layer was separated. The aqueous alkaline phase was extracted with $CH_2Cl_2$ ($2\times$). The $CH_2Cl_2$ layers were combined, washed with $H_2O$ ($2\times$), washed with saturated aqueous NaCl, and dried over anhydrous $Na_2SO_4$. The drying agent was removed by filtration and the filtrate was evaporated at reduced pressure leaving a foam which was dissolved in methanol (35 ml). The solution was cooled to 0° C. before being treated with a methanolic solution of HCl. The solution was concentrated to ca. 10-15 ml at which point crystallization began. After standing ca. 30 minutes, isopropanol was added and the flask was refrigerated. After 1-1.5 hour the product was collected by filtration. Recrystallization from methanol/isopropanol afforded 3-(2,2-diphenylethylamino)-2,5-dihydro-1H-2,4-benzodiazepine hydrochloride as colorless crystals: 2.53 g (67%), m.p. 243°-245° C.

Anal. Calcd. for $C_{23}H_{23}N_3 \cdot HCl$: C, 73.10; H, 6.40; N, 11.12. Found: C, 73.24; H, 6.41; N, 11.19.

EXAMPLE 18

A flask containing 3-methylthio-2,5-dihydro-1H-2,4-benzodiazepine hydroiodide (2.0607 g, $6.4357 \times 10^{-3}$ mole) and 3,3-diphenylpropylamine (1.3599 g, $6.4356 \times 10^{-3}$ mole) was immersed in an oil bath which had been heated to 155° C. The reaction mixture was stirred at between 155°-160° C. for ca. 1 hour. The resulting yellow glass was dissolved in methanol. Most of the methanol was evaporated and then isopropanol was added. The evaporation was continued and the solvent volume was periodically replenished by the addition of isopropanol until the solution became cloudy. Ether was then added and a solid slowly began to form. After standing two days, the precipitate was collected by filtration affording a colorless solid of the desired guanidine hydroiodide. This material was dissolved in a stirred two phase mixture of $CH_2Cl_2$ (50 ml) and 5 molar aqueous NaOH (40 ml, $2.0 \times 10^{-1}$ mole). After stirring overnight, the reaction was transferred to a separatory funnel where the $CH_2Cl_2$ layer was separated. The aqueous layer was extracted two times with $CH_2Cl_2$. The $CH_2Cl_2$ phases were combined, washed with $H_2O$, washed with saturated aqueous NaCl, and dried over anhydrous $Na_2SO_4$. The drying agent was removed by filtration and the filtrate was evaporated at reduced pressure leaving a colorless foam. The foam was then dissolved in methanol (20 ml) and the resulting solution was stirred and cooled to 0° C. To this solution was added a methanolic solution of HCl. After ca. 1 hour, the methanol was evaporated leaving an oil. This oil was dissolved in 2-butanone and ether was added until the solution became cloudy. After standing two days, the precipitate was collected by filtration. Recrystallization from methanol/2-butanone afforded tiny colorless needles: 1.47 g (58%), m.p. 178°–180° C. (decomp.).

Anal. Calcd. for $C_{24}H_{25}N_3 \cdot HCl$: C, 73.55; H, 6.69; N, 10.72. Found: C, 73.32; H, 6.69; N, 10.75.

What is claimed is:

1. A method for the treatment of angina comprising administering to a patient in need thereof, an antianginal amount of a compound of the formula:

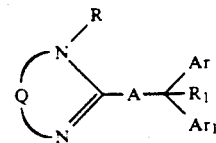

in which Q is represented by a substituent selected from the group consisting of $(CH_2)_n$ in which n is an integer from 2–10,

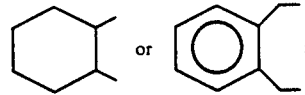

A is a substituent selected from the group consisting of $-NH-(CH_2)_m$ in which m is an integer from 0–5, a piperidino substituent, or a piperazino substituent; both Ar and $Ar_1$ are each independently represented by a phenyl ring, each of which may be optionally substituted with up to 3 substituents, each selected from the group consisting of halogen, $C_{1-4}$ alkyl, $C_{1-4}$ alkoxy, and trifluoromethyl; and R is represented by either hydrogen or a $C_{1-4}$ alkyl; $R_1$ is represented by hydrogen or a $C_{1-4}$ alkyl; the optical isomers and tautomers thereof; and the pharmaceutically acceptable acid addition salts thereof.

* * * * *